United States Patent
Lopez

(10) Patent No.: US 9,962,243 B1
(45) Date of Patent: May 8, 2018

(54) THERMOPLASTIC IMPRESSION TRAY WITH THREE FUNCTIONS

(71) Applicant: Oscar Lopez, Hialeah, FL (US)

(72) Inventor: Oscar Lopez, Hialeah, FL (US)

(*) Notice: Subject to any disclaimer, the term of this patent is extended or adjusted under 35 U.S.C. 154(b) by 0 days. days.

(21) Appl. No.: 15/615,750

(22) Filed: Jun. 6, 2017

(51) Int. Cl.
*A61C 9/00* (2006.01)
*A61C 13/00* (2006.01)

(52) U.S. Cl.
CPC ........ *A61C 9/0006* (2013.01); *A61C 13/0003* (2013.01); *A61C 2201/00* (2013.01)

(58) Field of Classification Search
CPC .......... A61C 9/006; A61C 9/00; A61C 13/003
See application file for complete search history.

(56) References Cited

U.S. PATENT DOCUMENTS

| | | | | |
|---|---|---|---|---|
| 4,235,594 A | * | 11/1980 | Schwartz | A61C 9/00 433/213 |
| 4,368,040 A | | 1/1983 | Weissman | |
| 4,401,616 A | * | 8/1983 | Wagner | A61C 9/0006 264/138 |
| 4,681,543 A | * | 7/1987 | Monroy | A61C 13/00 264/18 |
| 4,768,951 A | * | 9/1988 | Abiru | A61C 9/0006 433/37 |
| 5,266,031 A | * | 11/1993 | Marigza | A61C 19/05 433/214 |
| 5,961,325 A | * | 10/1999 | Van Handel | A61C 9/0006 433/213 |
| 6,077,075 A | * | 6/2000 | Bedard | A61C 13/04 264/18 |
| 6,196,840 B1 | * | 3/2001 | Zentz | A61C 9/0006 433/214 |
| 8,376,738 B2 | * | 2/2013 | Wagner | A61C 9/0006 433/6 |
| 8,998,615 B2 | | 4/2015 | Kim | |
| 9,498,310 B2 | | 11/2016 | Suga | |
| 9,545,294 B2 | | 1/2017 | Liebman | |
| 2005/0106529 A1 | | 5/2005 | Abolfathi | |
| 2006/0183080 A1 | * | 8/2006 | Nosov | A61C 9/0006 433/215 |
| 2007/0190488 A1 | * | 8/2007 | Rusler | A61C 13/0025 433/171 |
| 2008/0254406 A1 | * | 10/2008 | Wagner | A61C 9/0006 433/41 |
| 2011/0045442 A1 | * | 2/2011 | Adusimilli | A61C 9/00 433/201.1 |
| 2012/0179281 A1 | * | 7/2012 | Steingart | A61C 13/0004 700/97 |
| 2013/0216978 A1 | * | 8/2013 | Thompson | A61C 13/0004 433/199.1 |

(Continued)

*Primary Examiner* — Nicholas Lucchesi
*Assistant Examiner* — Shannel Wright
(74) *Attorney, Agent, or Firm* — Christopher J. Van Dam, PA; Chris Vandam

(57) ABSTRACT

A method for fabricating a denture using, among other devices, a semi-custom thermoplastic tray. The thermoplastic tray is customized over a mold of an edentulous ridge. The thermoplastic tray has a handle that it trimmed off after its use as a tray thereby converting the thermoplastic tray into a base plate for continued fabrication of the denture. This allows the denture to be completed in only a few days with the patient making a trip to the dentist for the initial fabrication steps and then a second time to pick the finalized denture.

1 Claim, 4 Drawing Sheets

(56) References Cited

U.S. PATENT DOCUMENTS

| | | | |
|---|---|---|---|
| 2014/0363785 A1* | 12/2014 | Monicelli | B29C 39/026 433/48 |
| 2015/0010879 A1* | 1/2015 | Kurthy | A61C 3/02 433/37 |
| 2015/0190216 A1* | 7/2015 | Suga | A61C 9/0006 433/213 |
| 2016/0158628 A1* | 6/2016 | Layzell | A61C 9/0006 128/862 |
| 2017/0071708 A1* | 3/2017 | Kohgo | A61C 13/01 |

* cited by examiner

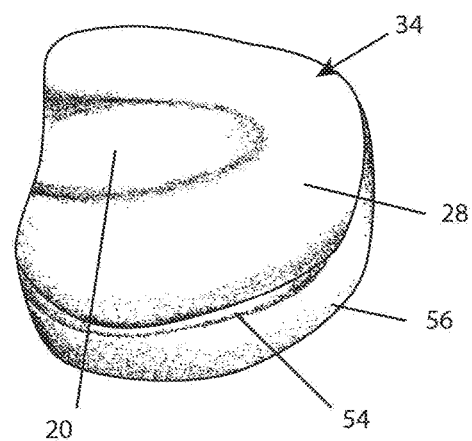
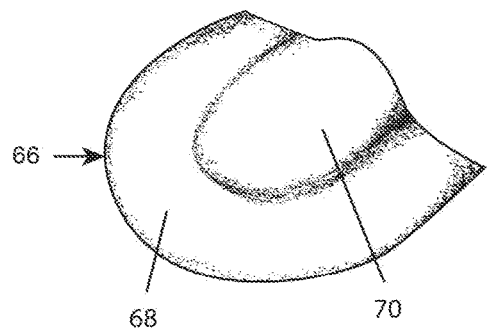
FIG 9.  FIG 10.
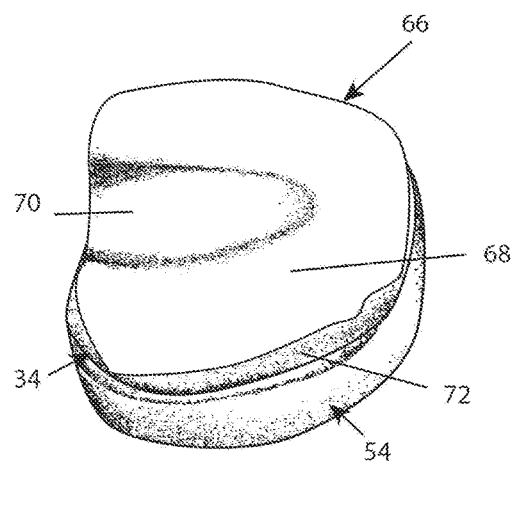
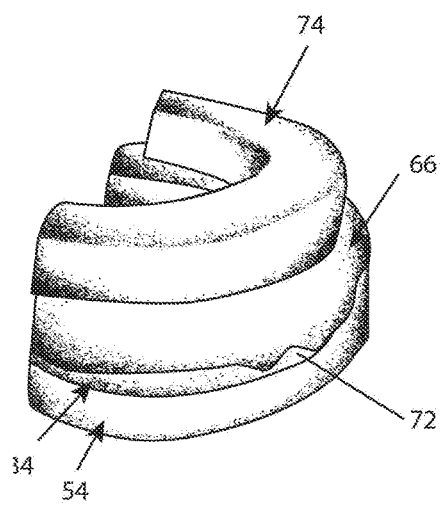
FIG 11.  FIG 12.

THERMOPLASTIC IMPRESSION TRAY WITH THREE FUNCTIONS

BACKGROUND OF THE INVENTION

1. Field of the Invention

The present invention relates to prosthodontics, and more particularly, to a method with associated apparatus to fabricate oral dentures with a thermoplastic dental impression tray with three functions.

2. Description of the Related Art

Several designs and methods for denture fabrication have been designed and used in the past. None of them, however, includes a means to drastically shorten the time required to properly fabricate and fit dentures using particular materials and processes.

Applicant believes that the closest reference corresponds to U.S. Pat. No. 8,376,738 issued to Wagner. However, it differs from the present invention because, although the Wagner device discloses a thermoplastic tray, it does not utilize the tray converted from use as a tray to a base for the fabrication of dentures. While this tray which in various steps of the method can be used as a temporary impression, a custom tray, and as a base plate. Wagner merely describes a tray that it shapeable but not as part of a method, including apparatus, that shortens the time needed to fabricate a set of dentures by maximizing the work that can be performed outside of the lab while the patient waits in the dental office.

Other patents describing the closest subject matter provide for a number of more or less complicated processes and features that fail to solve the problem in an efficient and economical way. None of these patents suggest the novel features of the present invention.

A brief abstract of the technical disclosure in the specification and title are provided as well for the purposes of complying with 37 CFR 1.72 and are not intended to be used for interpreting or limiting the scope of the claims.

Without limiting the scope of the invention, a brief summary of some of the claimed embodiments of the invention is set forth below. Additional details of the summarized embodiments of the invention and/or additional embodiments of the invention may be found in the detailed description of the invention below.

SUMMARY OF THE INVENTION

It is one of the main objects of the present invention to provide a hastened denture fabrication process, with related apparatus, to ease suffering of patients by reducing the amount of time dentures will be fabricated.

It is another object of this invention to provide a method and apparatus to allow more of the denture fabrication procedure or steps to occur in the dental office instead of multiple trips to a dental lab.

It is still another object of the present invention to provide a denture fabrication process and device to reduce the number of patient visits to the dental office while dentures are being prepared.

It is yet another object of this invention to provide such a process and related device that is inexpensive to practice and manufacture while retaining its effectiveness.

Further objects of the invention will be brought out in the following part of the specification, wherein detailed description is for the purpose of fully disclosing the invention without placing limitations thereon.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which they are illustrated and describes various embodiments of the invention.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 9 shows a perspective view of the thermoplastic tray fit over the mold of FIG. 7.

FIG. 10 shows a perspective view of a wax tray assembly.

FIG. 11 shows a perspective view of the wax tray assembly of FIG. 10 being fit over the thermoplastic tray.

FIG. 12 shows a perspective view of a bite block being fit onto the wax tray assembly.

DETAILED DESCRIPTION OF THE PREFERRED EMBODIMENT

Figure 1:
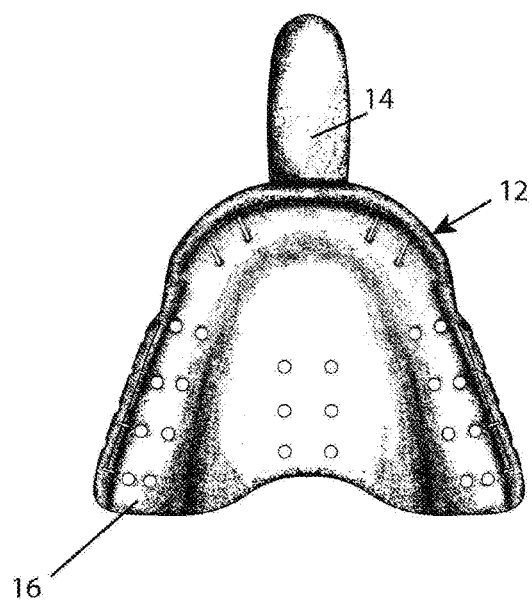
FIG. 1 shows a perspective view of a standard tray.

While this invention may be embodied in many different forms, there are described in detail herein specific embodiments of the invention. This description is an exemplary of the principles of the invention and is not intended to limit the invention to the particular embodiments illustrated and described.

For the purpose of this disclosure, like reference numerals in the figures shall refer to like features unless otherwise indicated or is obvious by context.

The subject device and method of use is sometimes referred to as the device, the invention, the denture, the denture assembly, the workup, the machine or other similar terms. These terms may be used interchangeably as context requires and from use the intent becomes apparent. The masculine can sometimes refer to the feminine and neuter and vice versa. The plural may include the singular and singular the plural as appropriate from a fair and reasonable interpretation in the situation.

Over a career of dentistry it became apparent how patients suffer as they lose their teeth. They can't properly chew their foods well and often times have difficulty swallowing too. Due to all this, often times patients limit themselves in the types of food they eat and maintain a semi solid and liquid diet in order to maintain their energy levels. Not only is it a physical disability but the dental research is well documented in showing that patients also suffer psychological traumas associated with edentulous patients not being able to smile properly because they are embarrassed and self-complexes associated to a lack proper mastication.

Using methods of the prior art, a full denture has an approximate time of completion of twenty-five to thirty five days depending on the laboratory and dentist's work load.

Throughout the fitting period, the amount of patient visits to the dentist's office that must be completed in order to sit a full denture on a patient averages approximately eight visits or more. During this process the patient is suffering.

Few dental practices have an in-house dental laboratory in order to better serve patients and to reduce the number of visits to help edentulous patients. Due to performing several steps traditionally done in a dental lab and at a dental office it is possible to reduce the number of patient visits down to two or three times consistently.

Most dentists do not do any dental lab procedures associated with prosthodontics at their offices, for example, the creation of custom trays and/or base plates. All the work usually gets sent to a dental laboratory. Because to the dentist, their time is more important than the costs associated with the process by a laboratory.

The present process and related device cuts the number of patient visits to the dental office thus reducing the time it takes to complete a full denture case whether it is a single denture, for example an upper or lower or a complete full denture case. All this results in greater savings not only to the patient because their number of visits to the dentist will be dramatically reduced and also by not having to miss work or schedule days off around appointment times.

It may also represent a savings to the dentist because their time is precious and this will give them more time to see and help other patients. Also it is monetarily efficient because of the reduction in the number of trips to the dental lab. In the end, the most important aspect is to reduce the amount of time patients suffer due to not having their teeth.

The following is an example of the steps needed for a dentist to make a patient's full dentures. In this example, we will build the maxillary or upper denture because the patient has his teeth in the mandible (lower set of teeth). This example is enabling and shows but one example of the process with related devices but the same concept/method can be applied to a full denture case.

The dentist will begin the case by taking a thorough and in-depth clinical history in order to determine what will be the best treatment option for the patient. Once the course of action has been determined and agreed upon by the patient, as in this particular example, a full upper denture will be fabricated for the patient.

We take a provisional impression of the upper edentulous ridge and the lower teeth as well with a standard plastic disposable impression tray. These disposable trays do not adapt perfectly to the patient edentulous ridge especially the lateral flanges because they are always too high or large and as a result displace the muscles of the mouth in the upper region. For upper dentures, the same theory is applied to inferior dentures as well with the floor of the mouth. The end result is that it creates a false impression of the patient's gums. We then take an impression of the lower teeth as well, but in this case we are somewhat less concerned how the lower muscles displace because the important aspect here is the actual lower teeth so that we can obtain a proper occlusal relation with the upper edentulous ridge. It is important for the patient to attain a good biting (occlusal) relation between the eventual upper teeth of the denture and his lower teeth so the patient's bite is in harmony.

This relation is in dentistry jargon is called "maxillomandibular relations for full dentures." These initial impressions are taken with a material called alginate. The alginate is mixed with the required amounts of water and mixed and poured onto the disposable impression trays. The filled tray is then taken to the patient's mouth in order to get the initial provisional impressions (upper and lower).

Once the provisional impressions are set, pour in the proper gypsum material which in this case is white plaster and get two provisional molds. One of which will be sent to the lab and the other will be kept for later use. If the dentist tries to do a denture with these provisional models it will be a total failure since this denture will not adapt perfectly to the patient's gum, or in dental terminology the edentulous ridge. This would cause great harm and discomfort to the patient since the denture is not properly adjusted for his/her gums.

Returning to the upper provisional impression, the dentist or the assistant will call the dental laboratory to pick this model in order to make an individualized model tray or commonly known in the dental community as a custom tray. The lab will send a messenger to pick the model. These trips back and forth between the dental office and dental lab have an associated cost of seven to ten dollars per trip.

Examining the prior art methods we can document the number of trips it will take for this patient to receive their completed dentures. The dental laboratory picks up the model and will construct the custom tray. This is the first trip.

This particular process takes long due to the method of construction. After it is complete the lab sends the custom tray back to the dentist's office. Of course the number of days in between can vary based on the dental laboratory's work load but typically takes a few days, anywhere from three to four days.

Then comes trip number two when the dentist receives the custom tray from the dental laboratory. The patient is scheduled for the next appointment to take a final impression of the upper edentulous ridge or gum. This impression is now taken on the custom tray and it is made with a silicon material called polyvinyl siloxane (PVS) also called vinyl polysiloxane (VPS) both terms are interchangeable and amply used in the dental community.

At this point in the process the dentist is done with the patient in the office and calls the dental lab to send the messenger to pick up the final impression on the custom tray. This is trip three of the partially completed denture. This time the lab will fill the impression with an extra hard yellow plaster in order to get their model. On this new model the lab will construct a base plate.

Over the base plate the lab will affix an occlusal bite block rim that is secured well with wax. This process requires that the dental technician waxes properly all the sides in order to make sure the bite block and the base plate are properly adjoined. The in-process denture is then sent to back to the dentist in trip number four.

The dentist then makes the necessary adjustments to the bite block by recording the mid line and other requisite measurements in order to align the teeth properly and then proceeds to record a bite with a specific wax usually shaped as a horseshoe. Usually bite registration wax is used. This wax will be slightly heated and then placed in the patient's mouth and instructed to bite. After biting down the bite relation between the upper model and the lower teeth is established. The lab is then summoned again to pick up for trip number five of the bite registration wax along with the bite block and the model of the inferior teeth taken in an earlier step which were saved. The dental lab will mount all these parts in an articulator.

The dental lab will now mount these parts in an articulator to mount the teeth and resend it back to the dentist in trip number six. The dentist can then try out the denture on the patient and if it fits well he then calls back the dental lab to pick the wax denture for trip number seven.

The dental lab then finishes the final denture and sends it back to the dentist in trip number eight. Again, the dentist has to schedule the patient once again so he can come in and try in his final upper denture.

Finally the dentist gives the patient the completed denture. A lot of time and days have gone by, typically anywhere from twenty-five to thirty-five days. These times depend whether there are no problems in the patients bite that the dental lab and dentist would be required to repeat to correct any of the aforementioned steps. If so, the number of days continue to accrue meanwhile the patient is still suffering.

Prior impression trays would not serve as a suitable base plate because they are too big or small. Because they are one-size-fits-most, the standard trays are not adaptable to the multitude of sizes of maxilla and mandibular edentulous ridges (gums).

The present invention is now described to contrast the above prior art methods of denture construction.

Start by making a mold with a thermoplastic impression tray selected from a set of various sizes in both maxillary and mandibular sizes. These could, for example be x-large, large, medium, small and x-small. Of course other sizes or numbers of sizes would also be effective. By having several size trays the fit can be much better than if only one size is available.

The thickness of these trays would be about 3 mm in its base while at the same time after the curvature of the flange it will end up about 2 mm. The handle will be about 3 mm thick. These are merely enabling examples and are not intended to be limiting. Other thicknesses could be equally effective.

The process does not require the dentist to adapt or adjust the tray in the patient's mouth as this is a difficult step in the process. The dentist never has a good view all the way down the gums of the patient in the back of the mouth. It's easier to see the front part of the edentulous ridge than the back part of the ridge (or gum). Therefore, the dentist needs to continuously heat the tray until it meets the requirements of the final adaptation which takes time.

To begin the process, the dentist will take an impression with one selected from the aforementioned 5 sizes of both top and bottom jaws basically which ever size the dentist determines is closest to the patient jaws. If the patient is completely edentulous the dentist could do a full set of dentures. These initial provisional impressions will be taken with alginate and filled up immediately with a white plaster and the alginate removed from the impression tray for continued use in the upcoming steps. These materials are intended to be enabling and not limiting. Other dental materials with similar performance characteristics could also be used effectively.

The patient can then sit in the waiting room for a few minutes while the models are formed. The models will be made from white plaster. This takes approximately fifteen minutes. The dental assistant does these tasks, thus freeing up the dentist to rotate to another patient in the meantime if he/she so desired.

When the fifteen minutes have elapsed and the white models are formed, the assistant takes those back to the dentist so they can be inspected. The dentist marks them gum line all around with a pencil or other marker. Now the tray just used which had the alginate removed is dipped into hot water, about fifty to sixty degrees Celsius, depending on the character of the tray material. Once placed in the hot bath, the thermoplastic tray now becomes pliable and adaptable to the white plaster model and any excess is trimmed and or cut off. If the tray is a bit too long then reheat and trim until it reaches the pencil marks.

After a clinical evaluation, if all looks good the tray is tried in the patient's mouth to ascertain its proper adaption. Now the final impression steps can begin. This impression is made with silicone-polyvinyl siloxane (PVS) also called vinyl polysiloxane (VPS), or other similarly performing material. We begin by first putting silicone on the top border of the flanges of the tray in order to facilitate the border molding movements which are essential in recording great clinical impressions.

The custom tray is removed and inspected to see if there are any high points. If it is, then this demonstrates that the custom tray is a bit long in that specific place and it is trimmed or reduced it with a lab carbide bur. All this simply means is that the tray is hitting an area where its not supposed to make contact hence its reduction. This step completed, the dentist then proceeds to fill the entire tray with silicone and take the final impression(s).

The impression this time is filled with a different gypsum, extra hard yellow plaster. Again, wait about fifteen minutes for this model to harden. Once again, the patient is asked to kindly go sit at the waiting room instead of finishing the dental appointment at that time. After the fifteen minutes have elapsed the model is now hard and it's separated from the tray and re-inspected. Immediately after, remove the impression silicone from the custom tray just like it was done on the first step with the alginate. Then we reheat the custom tray and further adapt the tray to the yellow stone model because this model represents a higher mold of the patient's oral cavity and there has greater anatomical details.

Then cut the handle of the tray with fine wheel disk. Then reduce this area where the handle was removed with a lab carbide bur until its smooth. This essentially converts the tray into a base plate. After this step is complete we now have a base plate. This essentially gives the invention three primary functions (initial temporary impression tray, custom tray, and base plate).

On top of the base plate a preformed wax sheet designed specifically to complement the size and shape of the custom tray we selected initially is placed. These pre-formed waxes will also come in five sizes like the trays as well. By way of example, x-large, large, medium, small and x-small waxes may be supplied in a kit or otherwise available. A different number, name or sizes of wax can also be effective.

One of the reasons to use the pre-formed wax at this step is to cover all the perforations of the custom tray since the base plate cannot have any holes as these will extend to the final denture. It also makes the task of fitting the wax onto the base plate (formerly the custom tray) easier for the dentist to accomplish from the conventional methods already seen in the denture making process.

The preformed wax setup is then almost complete. This translates to a huge time savings not only to the dental lab technician because the technician would have to wax this part manually, little by little, until it's all complete. With our preformed wax this process takes significantly less time, benefiting both patient and dentist.

Next, over this preformed wax an occlusal bite block rim is fitted and its proper measurements are applied as the bite block rim(s) to simulate the patient's gums. With a heated instrument both waxes are sealed together and smooths. The patient can then return to the treatment chair. The dentist will now make the necessary adjustments to the bite block by recording the mid line and the ala-tragus line otherwise known as Camper's Line and all other measurements.

The patient is asked to smile so that the proper steps are taken in order to evaluate the model thus far. It is also marked so that the right amount of teeth will show when the patient smiles. Basically, where the lip stops when one smiles is the proper point because this determines the length of teeth and the teeth placement on the denture.

The mid-line is marked in order to know exactly where the central teeth will be placed in the middle of mouth. This helps center the denture in the patient's mouth. Then the dentist makes sure the bite block is completely parallel with floor.

The dentist will record a bite with a special wax, shaped as a horseshoe, called bite registration wax. This wax will be slightly heated and then placed in the patient's mouth and instructed to bite. After they bite the entire bite relation between the upper model and the lower teeth is completed.

At this point everything that can be done in the dental office is finished and the patient can go home. Now, for the first time in this process the dental laboratory is called to pick up the bite block along with the bite registration and the inferior model. The inferior model is the one saved originally from earlier in the process. From here the dental lab will mount all this in an articulator and proceed to put the teeth to the model in wax.

It should now be apparent that the patient has been saved about four trips to the dental office through this point. Now finishing the denture in five to six days is a reality. If the Dentist would have a dental lab at the office they would be able to complete to the denture in 1-2 days.

The dental laboratory picks up the bite block, in trip number one to the lab in this new process, along with the bite registration and the inferior model. The dental lab mounts the teeth on wax model and sends it back to the dentist in trip number two.

Then the dentist schedules the patient for the complete denture wax try-in and test what lab has just sent back. The dentist makes sure everything is in order and where it's supposed to be in and sends it back to the dental laboratory in trip number three. This is so the lab can finish the denture. Then its sent back to the dentist in trip number four. Once again the patient is scheduled to come into the dental office and pick up the full denture.

In summary, this updated process of impression tray converted to a custom tray and then converting to a base plate is a reliable way for dental practitioners to cut the amount of time it takes to complete a full denture. Patients will have their set of teeth (denture) in about five to seven days.

The patient is then able to continue their proper regular physiological functions of food mastication and the creation of food bolus. Being able to properly prepare the food bolus via mastication aids in proper digestion and enables the patients to eat different food sources and not be limited to semi-soft diets. Aesthetically, patients' will increase their self-esteem thereby creating a measurable generalized life improvement overall.

To summarize the process of denture fabrication, a pair (upper and lower) of thermoplastic impression trays with five upper sizes: x-large, large, medium, small, x-small are provided. The corresponding lower sizes of the (mandibular) thermoplastic impression trays also are available in x-large, large, medium, small, x-small. These can either be perforated or non-perforated with a thickness that can vary between about 2.5 mm to 4 mm. Following this the dentist will construct the custom tray. This custom tray will have a handle which will have to be fused (attached) and later removed (via cutting or other method) which will serve as what's called the base-plate. Along with this, there will be available a set of preformed wax plates which will be provided in the same sizes as the custom tray. Similar to the trays, the wax plates are sized to accommodate the whole process of the wax up of the denture. This is equivalent to two steps in the conventional process of making dentures for the patient.

This invention's trays could also be used in the beginning process of by taking the initial impression. This perforated tray is used to first take the impression with alginate and then pour our first hard model. Then remove the alginate and continue to use the perforated tray to make the custom tray that will be further adapted to the aforementioned model via heating the (thermoplastic) tray and adapting fully to the dentists' satisfaction to fit the custom tray. After the custom tray is made then take an impression with vinyl polysiloxane and create the final model in extra hard yellow plaster. This will be used to construct the ultimate denture. Now with the yellow plaster model the dentist continues to make the base plate.

Using one of the five sizes of preformed wax (approximately one mm in thickness) and put over the base plate. Once the wax is united with the base plate the dentist will put on the wax bite block. With this process three steps are saved over the prior art process because the tray is used as a pseudo disposable tray (in this case not disposable). The tray is used to create the custom tray. It is then used it again to create the base plate. Therefore, all these steps can be done with a single tray.

A base plate could also be used that is approximately anywhere from 2.5 to 3 mm of the thermoplastic material or other relevant material to construct the custom tray and then take the final impression and then pour our model in extra hard yellow plaster. Following this step the preformed wax with a thickness of about 0.5 to 1.5 mm over the base plate and proceed with the traditional following steps as usual.

It is thus revealed that this invention is related to an impression tray that has three functions: first, it could be used to record a temporary impression with Alginate; second, after removing the alginate material it could be used as a custom tray in order to have a final impression and corresponding model; and third, after cutting the handle from the custom tray it could be used a base plate in the formation of a final denture.

Throughout this description specific materials are sometimes named. These are enabling examples and are not intended to be limiting. It should be understood that there are many generic and brand name materials available and suitable to such dental use. It is the characteristics of the named materials that should be a guide to achieve similar performance as the named materials. The terms dentist and technician are used interchangeably throughout the specification because some technicians have skill levels of that approach those of the dentist under which they work.

Referring now to the drawings, where the present invention is generally shown throughout the drawings and referenced in the specification, it can be observed that it basically includes a tray assembly 12, a handle 14, a channel 16, an impression 18, a ridge impression 20, a palate impression 22, a positive mold 24, a palate 26, a ridge mold 28, a gum line 30, a foundation 32, a tray assembly 34, a channel 36, a palate 38, a handle 40, a wall 42, an edge 44, a gap 46, an impression assembly 48, a palate 50, a gum impression 52, a mold 54, a ridge mold 56, a palate mold 58, a base 59, a line 60, a cutoff tool 62, a gap 64, a wax plate assembly 66, a ridge 68, a palate 70, a gap 72, a bite block 74, registration marks 76 and a biting wax 78.

The figures in the drawings are representative and may summarize parts of the process that are well known to dental technicians. The figures are in sequence of the steps taken by the technician and lab during the fabrication process.

FIG. 1 is generally an example of a standard tray assembly 12. It has a handle 14 to aid the dentist taking an oral impression. The channel 16 is "U" shaped to approximate the jaw line. Tray assemblies come in a variety of shapes and configurations for different sized mouths and for upper and lower jaws. The dentist, as in the prior art, selects the appropriate tray assembly 12 for that patient.

Figure 2:
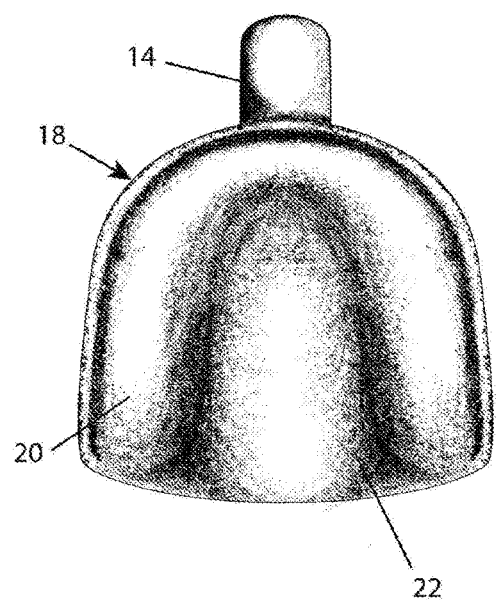
FIG. 2 shows a perspective view of an impression with the tray of FIG. 1.

In FIG. 2 an impression 18 of the patient's mouth is taken. The channel 16 of the tray assembly 12 is loaded with an impression material such as alginate. As the alginate solidifies, the impression 18 forms revealing the ridge impression 20 and the palate impression 22. The handle 14 helps the dentist pry the solidified impression 18 from the patient's mouth.

Figure 3:
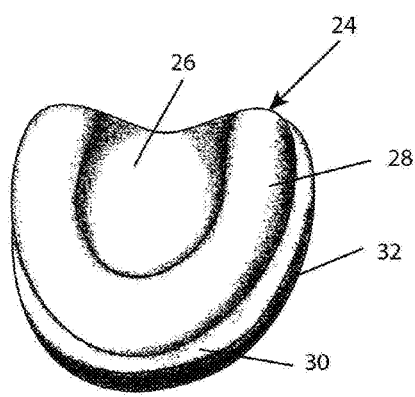
FIG. 3 shows a perspective view of mold made from the impression of FIG. 2.

FIG. 3 shows a positive mold 24 made from the impression 18 in the prior step. The positive mold 24 is typically poured with white plaster. Other molding materials suitable for dental use may also be used as appropriate to make a positive mold 24.

The positive mold 24 should closely approximate the form of the patients mouth. The palate 26 and ridge mold 28 should be clearly identified. Additional plaster is poured into the impression 18 to account for a foundation 32. The dentist marks an estimated gum line 30 around the ridge mold 28. The gum line 30 is used later in the process to establish the peripheral edge of the final denture.

Figure 4:
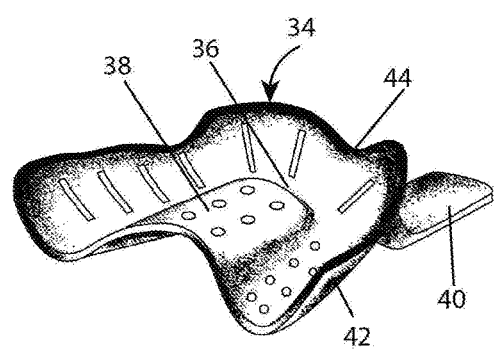
FIG. 4 shows a perspective view of a thermoplastic tray.

FIG. 4 shows a tray assembly 34 made of a thermoplastic resin. In one version of the invention several different sizes of tray assemblies 34 are available to the dentist. The most appropriate size is selected by the dentist so that minimal adjustment and fitting is needed.

A handle 40 is provided to aid the dentist maneuvering the tray assembly 34. The edge 44 is dimensioned to correspond to the gum line 30 and may be stretched or trimmed to fit the gum line 30 along the wall 42.

The tray assembly 34 is preferably made from a thermoplastic resin material, or other material with similar performance characteristics. The tray assembly 34 may need some adjustment in shape and dimension to fit closely over the positive mold 24. The nature of the thermoplastic is that of being softened and malleable when heated is desired to allow the dentist to warm the tray assembly 34 to stretch and press and trim as needed to fit the positive mold 24 and form the edge 44 along the gum line 30. The heat is typically supplied by a warm water bath, torch, hot air gun or other similar such device.

Generally, when fitting the tray assembly 34 onto the positive mold 24 it is better to start with a tray assembly 34 sized slightly smaller than needed to cover the edentulous ridge mold 28. This is because it is easier to stretch with the fingers to adjust the fit rather than trim a larger size to fit. This is, however, the prerogative of the dentist.

Figure 5:
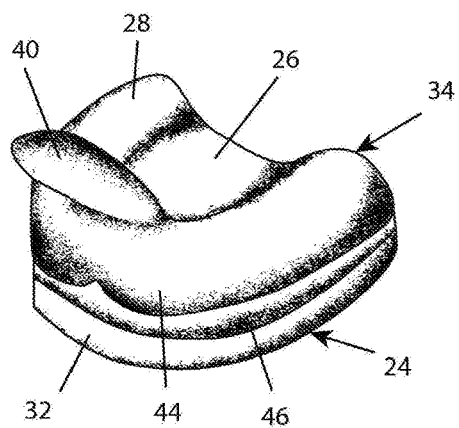
FIG. 5 shows a perspective view of the thermoplastic tray in FIG. 4 fit over the mold of FIG. 3.

FIG. 5 shows the tray assembly 34 that has been fitted over the positive mold 24. Notice that the edge 44 is trimmed along the gum line 30 (not visible in FIG. 5) so that there is a gap 46 between the foundation 32 and the edge 44. The gap 46 is needed for a comfortable final fit of the denture on the patient so that the edge of the denture against the gums or gingiva does not over extend and dig into the gingiva uncomfortably. This is the point where the final fitting of the tray assembly 34 over the positive mold 24 is completed.

An advantage of fitting this custom tray assembly 34 over the positive mold 24 over the prior art is that it can be fit while outside of the patient's mouth. To get a custom tray of this detailed resolution while inside the patient's mouth would be nearly impossible. This is particularly true for the rear parts of the patient's mouth. Also, when out of the patient's mouth there is little risk of scalding when heating the tray assembly 34 during fitting. Further, significantly more hand pressure can be applied to the tray assembly 34 against the positive mold 24 when on the dentist's bench.

Figure 6:
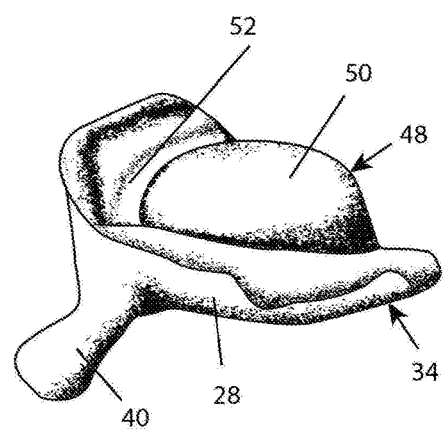
FIG. 6 shows a perspective view of an impression made with the thermoplastic tray of FIG. 4.

In FIG. 6 the tray assembly 34, now a custom tray, is filled with impression material such as silicone and an impression assembly 48 is taken of the same jaw of the patient as in the prior steps described above. The process of refining the fit with more precise molds and impressions will help result in a highly precise and personalized fit of the denture which will lead which will lead to a better clinical adaptation improving fit and denture performance.

Similar to the earlier impression 18, the impression assembly 48 clearly defines the palate 50 and the gum impression 52. The impression assembly 48 made in the customized tray assembly 34 is a finely crafted negative of the patient's edentulous ridge.

Figure 7:
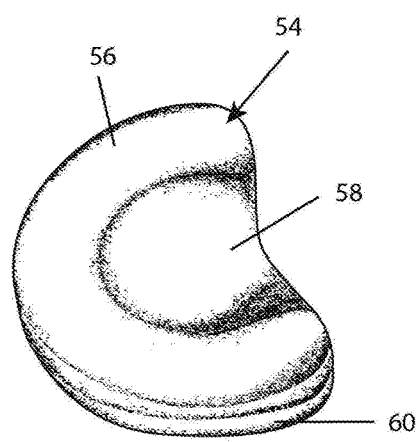
FIG. 7 shows a perspective view of a mold made from the impression of FIG. 6.

FIG. 7 shows a mold 54 made from the impression assembly 48. Generally the mold 54 is made of a hard and rigid material such as yellow stone. However, other available materials with similar performance characteristics could be effectively used.

The mold 54 is now has refined details over the earlier positive mold 24. On mold 54 details of the ridge mold 56 and the palate 58 closely match the actual anatomy in the patient's mouth The mold 54 is built with an integral base 59 so that it can be held in an articulator later during the finishing stages.

Figure 8:
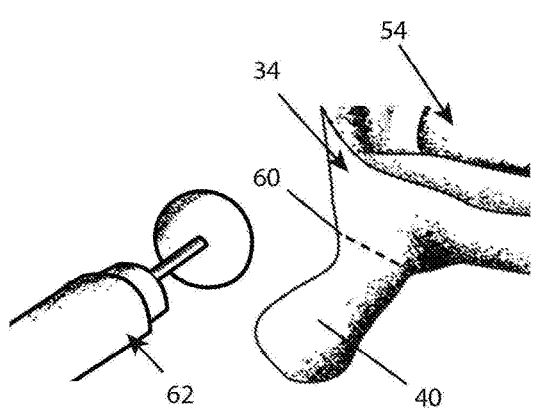
FIG. 8 shows a perspective view of trimming the handle off of the thermoplastic tray.

FIG. 8 shows an important inventive step in the process. The tray assembly 34 is cut to remove the handle 40 at the imaginary line 60. The line 60 is located where the handle 40 intersects with the balance of the tray assembly 34. The ridge mold 54 may be held into the tray assembly 34 during the cutting process. In this example a rotary cutoff tool 62 makes short work of trimming off the handle 40. Any cutting or trimming tool suitable for the material could also be effective.

Smoothing and trimming the tray assembly 34 after the handle 40 is removed is generally performed. Heat can be applied to soften the thermoplastic material of the tray assembly 34 if needed to trim with a blade or other minor refinements.

With the handle 40 removed the tray assembly 34 is functionally converted into base plate onto which the denture fabrication is built. This is an important step in the process because it saves the time the dentist would need to send the assemblies made so far back to the lab for creation of a new custom base plate before the rest of the process can continue.

In FIG. 9 the tray assembly 34, now a base plate, is able to fit over the mold 54. The slight gap 64 is assured between the mold 54 and tray assembly 34 so that the final denture does not dig into the gums of the patient causing a potentially uncomfortable situation and allowing for the lab to finally fit the denture.

FIG. 10 is a preformed wax plate assembly 66 fabricated of a sheet of dental wax formed into a shape to complement the size and shape of the tray assembly 34. The wax plate assembly 66, like the tray assembly 34, has a ridge 68 that matches the ridge mold 28 and the palate 70 that matches the palate 26.

The wax plate assembly 66 may be provided to the dentist in a variety of premade sizes to match the several sizes in which the tray assembly 34 is provided. This can save the dental lab technician time in custom fabrications and sizing of the wax plate assembly 66.

FIG. 11 shows the wax plate assembly 66 fit over the tray assembly 34 that is fitted onto the mold 54. The dentist may need to stretch, press and trim the wax plate assembly somewhat to get the wax plate assembly 66 to tightly conform to the contours of the ridge mold 56 and palate 58 that comprise the customized mold 54. Sometimes the dentist may apply some heat to soften the wax plate assembly 66.

Notice that the gap 72 remains present to ensure there is sufficient relief on the final denture to avoid digging into the gums of the patient.

FIG. 12 demonstrates the next step in the process where a bite block 74 is adhered to the ridge 68 of the wax plate assembly 66. The bite block 74 is typically made of wax but could also be made of other materials suitable and known in the dental industry to act as a bite block. If the bite block 74 is wax, it can be heated on the bottom surface that contacts the ridge 68 so that these two wax structures fuse together.

As with the wax plate assembly 66, tray assembly 34 and some other parts, the bite block rim 74 may be provided to the dentist in several sizes. The dentist may then select the size most similar to the dimensions of the ridge 68 so that customization is minimized. This also has the effect of speeding up the process.

Figure 13:
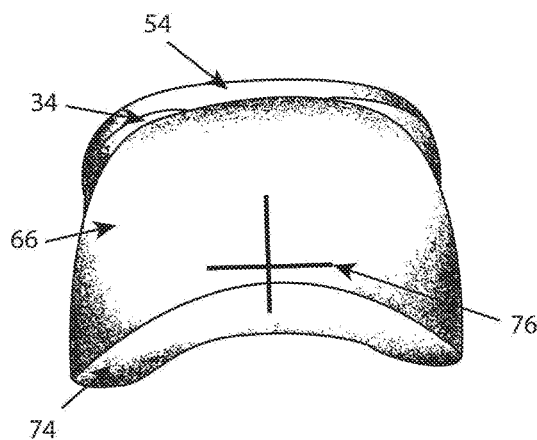
FIG. 13 shows a perspective view of an example of fitting the denture assembly with registration marks.

FIG. 13 shows the bite block 74 after it has been shaped and smoothed to seamlessly fit onto the wax plate assembly 66. The bite block 74 is then tested for fit inside the patient's mouth. The midline and smile line are defined with registration marks 76 drawn or carved on the bite block 74. The midline marks where the central incisors will meet when those teeth are finally fitted in the denture. The smile line determines how much of the teeth are exposed when the patient smiles. The placement of the registration marks 76 is part of the artistic expression of the dentist to get real looking dentures.

Figure 14:
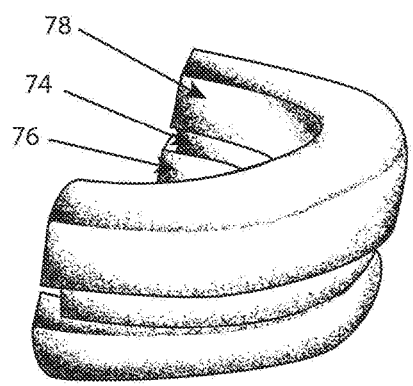
FIG. 14 shows a perspective view of a biting wax being fit onto the denture assembly.

FIG. 14 shows the process thus far with the addition of a layer of biting wax 78 adhered to the upper layer of the bite block 74. The biting wax 78 can be heated to fuse it onto the bite block 74. The assembly including the tray assembly 34 (now functioning as a custom base plate) and the several wax layers are removed from the mold 54. This assembly is placed into the patient's mouth and the patient is instructed to bite down to mark the biting wax 78 with the patients opposing teeth.

These bite marks on the biting wax 78 are the indication to the lab of where to place the teeth on the denture. This ensures that the teeth in the denture correspond appropriately to the patient's opposing teeth, whether natural or denture.

The entire process so far has been completed in one day in the dentist's office. The patient only needs to make the one appointment and one visit. What formerly took the patient several trips to the dentist's office and the denture-in-progress several trips to the lab, now has taken only a few hours.

Figure 15:
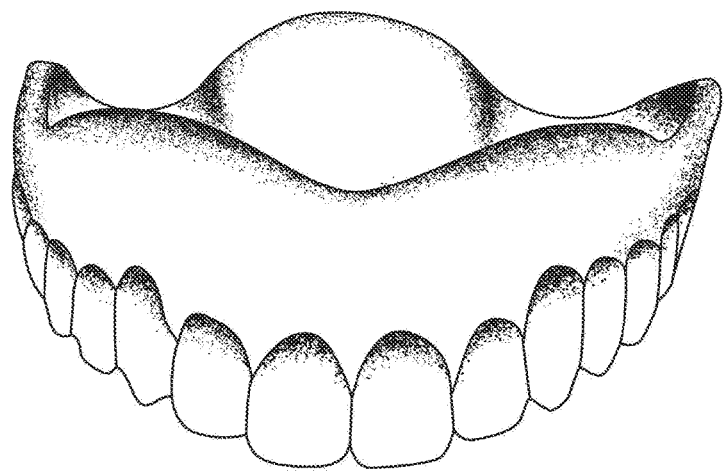
FIG. 15 shows a perspective view of a completed denture assembly.

The assembly thus far is then sent to the dental lab, typically outside of the dentist's office for the first time in this process. The lab uses conventional process to form the final, finished denture as exemplified in FIG. 15.

The patient and the final denture both return to the dentist's office for a final check for fit and comfort. If needed, the dentist can make fine adjustments. Then the patient is sent home with a new smile.

A version of the invention can be fairly described as a method for denture fabrication comprised of the steps in particular order: take a first impression of an edentulous ridge with a disposable or multi-function thermoplastic impression tray that best fits the anatomy of the patient. Then form a first positive mold from the first impression. A set of thermoplastic trays is provided having differing predetermined dimensions. Each thermoplastic tray in the set of thermoplastic trays includes a handle. Select a thermoplastic tray from the set of thermoplastic trays to approximately fit the first positive mold. Fit the thermoplastic tray to the positive mold by heating to stretch or trimming until there is a uniform gap between the thermoplastic tray and a gingiva of the edentulous ridge between about one millimeter and one point five millimeters, but this can be up to about five millimeters if needed. Take a second impression of the edentulous ridge with the thermoplastic tray. Form a second positive mold from the second impression. Trim the handle off of the thermoplastic tray to convert the thermoplastic tray to a baseplate. Form a wax plate to conform to the baseplate. Affix a bite block to the wax plate and form a ridge. Place the baseplate onto the edentulous ridge and make alignment marks on the bite block or wax plate. Affix a biting wax to the bite block. Soften the biting wax with heat and take a bite impression of a set of teeth or dentures opposing the edentulous ridge. Deliver the second positive mold and baseplate with biting wax, wax plate and bite block to a dental lab for completion of the denture using traditional methods.

In another example, the invention can be fairly described as a device for denture fabrication comprised of a semi-custom tray. The semi-custom tray includes a handle affixed to a middle edge of a ridge of the semi-custom tray. The semi-custom tray is fabricated of a thermoplastic material that can be shaped onto a mold after heating in a water bath. After an edentulous impression is made with the semi-custom tray the handle is removed thereby converting the semi-custom tray into a baseplate. The baseplate is then used as the foundation for fabrication of a denture model.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for denture fabrication for a patient comprised of the steps in particular order:

providing a set of thermoplastic trays having differing predetermined dimensions, each thermoplastic tray comprising the set of thermoplastic trays includes a handle;

selecting a thermoplastic tray from the set of thermoplastic trays to approximately fit an anatomy of the patient's edentulous ridge;

taking a first impression of an edentulous ridge with the selected thermoplastic impression tray;

forming a first positive mold from the first impression;

fitting the selected thermoplastic impression tray by heating to stretch or trimming the selected thermoplastic impression tray until there is a uniform gap between the selected thermoplastic impression tray and a gingiva of the edentulous ridge modeled on the first positive mold in a range of 1 millimeter and 5.0 millimeters;

taking a second impression with an impression material of the patient's edentulous ridge with the selected thermoplastic impression tray;

forming a second positive mold from the second impression;

separating the impression material from the selected thermoplastic impression tray;

removing the handle off of the selected thermoplastic impression tray to convert the selected thermoplastic impression tray to a baseplate;

fitting the baseplate to the second positive mold by heating to stretch or trimming the baseplate;

forming a wax plate to conform to the baseplate;

affixing a bite block to the wax plate and form a ridge;

placing the baseplate onto the patient's edentulous ridge and make alignment marks on the bite block;

affixing a biting wax to the bite block;

softening the biting wax with heat and take a bite impression of a teeth opposing the edentulous ridge;

delivering the second positive mold, baseplate with biting wax, wax plate and bite block to a dental lab for completion of the denture.

\* \* \* \* \*